US00PP09943P

United States Patent [19]

Cornelis

[11] Patent Number: Plant 9,943

[45] Date of Patent: Jul. 1, 1997

[54] SPATHIPHYLLUM PLANT NAMED STEPHANIE

[75] Inventor: Daniel Cornelis, Merelbeke, Belgium

[73] Assignee: Milestone Agriculture Inc., Apopka, Fla.

[21] Appl. No.: 628,952

[22] Filed: Apr. 8, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—C. A. Whealy

[57] ABSTRACT

A distinct cultivar of Spathiphyllum plant named Stephanie, characterized by its numerous leaves and side shoots give a dense full appearance; rapid growth rate; dark green glossy, large leaves that are held horizontal to the petiole; rounded pure white spathes; numerous large flowers that are positioned 10 to 15 cm above the foliage on strong and erect peduncles; and long-lasting flowers.

1 Drawing Sheet

The present invention relates to a new and distinct cultivar of Spathiphyllum plant, botanically known as Spathiphyllum, and hereinafter referred to by the cultivar name Stephanie.

The new cultivar is a product of a planned and controlled breeding program conducted by the inventor in Merelbeke, Belgium. The new cultivar originated from a deliberate cross by the inventor between the Spathiphyllum cultivar Pallas (not patented) as the female or seed parent and the Spathiphyllum cultivar Gigant (disclosed in U.S. Plant Pat. No. 7,657) as the male or pollen parent. The cultivar Stephanie was discovered and selected by the inventor as a plant within the progeny of the state cross in a controlled environment in Merelbeke, Belgium.

Asexual propagation, by division of the new cultivar at Merelbeke, Belgium, has shown that the unique features of this new Spathiphyllum plant are stable and reproduced true to type in successive generations of asexual propagation.

The new Spathiphyllum has not been observed under all possible environmental conditions. The phenotype may vary somewhat with variations in environment such as temperature and light intensity, without, however, any variance in genotype. The following observations, measurements and comparisons describe plants grown in Kwintsheul, The Netherlands, in 19-cm containers in a glass greenhouse with an average day temperature of 22 C., an average night temperature of 20 C., and a light level of 200 to 225 lux.

The following traits have been repeatedly observed and are determined to be the unique characteristics of Stephanie. These characteristics in combination distinguish Stephanie as a new and distinct cultivar:

1. Numerous leaves and side shoots give a dense full appearance.
2. Rapid growth rate, vigorous.
3. Dark green, glossy, large leaves are held horizontal to the petiole.
4. Rounded pure white spathe.
5. Numerous large flowers that are positioned 10 to 15 cm above the foliage on strong and erect peduncles.
6. Long-lasting flowers.

The new Spathiphyllum can be compared to its seed parent cultivar, the cultivar Pallas, and is different from the cultivar Pallas in the following characteristics:

1. Plants of the cultivar Stephanie are larger than plants of the cultivar Pallas.
2. Plants of the cultivar Stephanie have broader leaves than plants of the cultivar Pallas.
3. Plants of the cultivar Stephanie have larger spathes than plants of the cultivar Pallas.

4. Plants of the cultivar Stephanie flower earlier than plants of the cultivar Pallas.

The new Spathiphyllum can be compared to its pollen parent cultivar, the Cultivar Gigant, and is different from the cultivar Gigant in the following characteristics:

1. Plants of the cultivar Stephanie have more side shoots and are fuller and denser than plants of the cultivar Gigant.
2. Plants of the cultivar Stephanie are arching and spreading whereas plants of the cultivar Gigant are upright and not spreading.
3. Leaves of plants of the cultivar Stephanie are darker green and glossier than leaves of the cultivar Gigant.
4. Lower leaves of plants of the cultivar Stephanie maintain dark green color whereas lower leaves of plants of the cultivar Gigant become chlorotic with age.

The accompanying colored photograph illustrates the overall appearance of the new cultivar, showing the colors as true as it is reasonably possible to obtain in colored reproductions of this type. The photograph comprises a top perspective view of a typical potted plant of Stephanie.

In the following description, color references are made to The Royal Horticultural Society Colour Chart except where general terms of ordinary dictionary significance are used.

Botanical classification: Spathiphyllum cultivar Stephanie.

Parentage:

*Seed or female parent.*—Spathiphyllum cultivar Pallas.

*Pollen or male parent:*—Spathiphyllum cultivar Gigant (U.S. Plant Pat. No. 7,657).

Propagation: By division or by tissue culture.

Plant description:

*Plant shpae.*—Upright, inverted triangle, symmetrical.

*Growth habit.—Erect when young, becoming outwardly arching as leaves develop. Numerous side shoots give plants a full, dense appearance. Relatively large plants, appropriate for* 19-cm containers.

*Plant height.*—70 to 100 cm from soil level to top of leaf plane.

*Plant vigor.*—Rapid growth rate, vigorous.

*Crop time.*—Twenty-five weeks are usually required from planting of a young plant to a finished 19-cm container.

*Rooting habit.*—Freely branching, numerous fleshy roots with finer lateral roots.

*Foliage description.*—Leaf shape: Young: Narrowly ovate. Mature: Ovate, rounded. Leaf length: About 39.5 cm. Leaf width: About 19 cm. Margin: Entire. Leaf surface: Flat, not drooping. Leaf tip: Acuminate. Leaf base: Obtuse. Leaf aspect: Mature leaves held perpendicular to petiole, 90° angle. Leaf texture: Leathery, smooth, glabrous. Leaf color: Young, top side: Darker than 144A, glossy. Young, under side: Greener than 146C. Mature, top side: 147A, glossy. Mature, under side: 137A. Venation: Top side: 137C, sunken. Under side: 137C, prominent. Petiole length, primary shoot: 50 to 70 cm. Petiole diameter, primary shoot, just below geniculum: About 5 mm. Geniculum diameter, primary shoots: About 6 mm. Petiole wing, primary shoots: Apparent on lower 90% of mature leaf petiole. Petiole color: Young: 144A. Mature: Winged area: 137A. Above winged area: 137A. Geniculum: 137C.

Flower description:

*Flower arrangement.*—large flat spathe with spadix held 10 to 15 cm above the foliage. Numerous flowers arise from leaf axils.

*Flower longevity.*—Flowers are long-lasting, generally maintaining white color for 12 to 15 weeks on the plant depending on light and temperature levels.

*Spathe.*—Shape: Ovate, rounded. Size: Length: About 13.5 cm. Width: About 9 cm. Aspect: After unrolling, spathe is flat. Color: Before unrolling: White (155D). Open flower: White (155D) and shiny, spathe becomes green (144A) with age.

*Spadix.*—Size: Length: About 6.5 cm. Diameter: About 13 mm. Color: Initially yellow white (8D), becoming more yellow (8C) and eventually green with age.

*Peduncle.*—Aspect: Strong and erect. Size: Length: 80 to 115 cm. Diameter: 5 mm. Color: 144A.

Disease resistance: No known Spathiphyllum diseases observed to date on plants grown under commercial greenhouse conditions.

Seed development: Seed development has not been observed

It is claimed:

1. A new and distinct cultivar of Spathiphyllum plant named Stephanie, as illustrated and described.

* * * * *

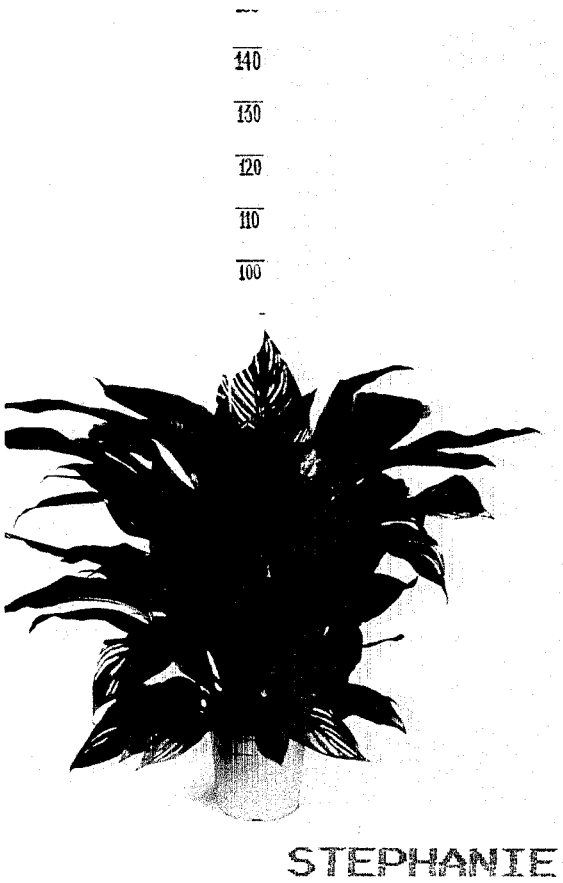
140
130
120
110
100
STEPHANIE